United States Patent [19]

Lindner et al.

[11] Patent Number: 5,023,260
[45] Date of Patent: Jun. 11, 1991

[54] SUBSTITUTED URACILS, PROCESSES FOR THEIR PREPARATION AND THEIR USE AGAINST PARASITIC PROTOZOA

[75] Inventors: Werner Lindner, Cologne; Axel Haberkorn, Wuppertal, both of Fed. Rep. of Germany

[73] Assignee: Bayer Aktiengesellschaft, Leverkusen, Fed. Rep. of Germany

[21] Appl. No.: 497,469

[22] Filed: Mar. 22, 1990

[30] Foreign Application Priority Data

Apr. 13, 1989 [DE] Fed. Rep. of Germany ....... 3912100

[51] Int. Cl.⁵ .................. A61K 31/505; C07D 239/52
[52] U.S. Cl. .................................... 514/269; 514/274; 544/310; 544/311; 544/312
[58] Field of Search ....................... 544/310, 311, 312; 514/269, 274

[56] References Cited

U.S. PATENT DOCUMENTS 3,017,322  1/1962  Ursprung ............................ 514/269
4,005,218  1/1977  Janssen et al. ....................... 514/521
4,578,402  3/1986  D'Silva ............................... 558/404

FOREIGN PATENT DOCUMENTS 2509037  9/1976  Fed. Rep. of Germany .

Primary Examiner—Cecilia Shen
Attorney, Agent, or Firm—Sprung Horn Kramer & Woods

[57] ABSTRACT

A substituted uracil useful for combating parasitic protozoa of the formula

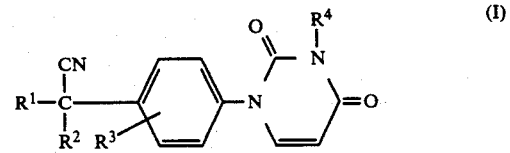

in which
$R^1$ represents a carbocyclic aromatic or heteroaromatic radical, which are optionally substituted,
$R^2$ represents H; or alkyl, alkenyl, alkinyl or aralkyl, each of which are optionally substituted,
$R^3$ represents one or more identical or different hydrogen, halogen, alkyl, halogenoalkyl, alkoxy, alkylthio, halogenoalkoxy, halogenoalkylthio, cyano, alkoxycarbonyl, alkylsulphonyl or halogenoalkylsulphonyl radicals,
$R^4$ represents hydrogen; or a straight-chain, branched or cyclic alkyl, alkenyl, alkinyl or aralkyl, each of which are optionally substituted.

4 Claims, No Drawings

SUBSTITUTED URACILS, PROCESSES FOR THEIR PREPARATION AND THEIR USE AGAINST PARASITIC PROTOZOA

The present invention relates to new substituted uracils, to processes for their preparation, to intermediates for carrying out these processes and to their use against parasitic protozoa.

The use of F-substituted uracil for combating coccidia is known. However, the effect of this compound is not satisfactory in every case (U.S. Pat. No. 3,017,322).

The present invention relates to

1. New substituted uracils of the general formula (I)

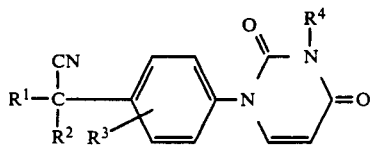

in which $R^1$ represents aromatic or heteroaromatic radicals, which are optionally substituted, $R^2$ represents H, alkyl, alkenyl, alkinyl or aralkyl, which are optionally substituted, $R^3$ represents one or more identical or different radicals from the group comprising hydrogen, halogen, alkyl, halogenoalkyl, alkoxy, alkylthio, halogenoalkoxy, halogenoalkylthio, cyano, alkoxycarbonyl, alkylsulphonyl and halogenoalkylsulphonyl, $R^4$ represents hydrogen, a straight-chain, branched or cyclic alkyl radical, alkenyl, alkinyl or aralkyl, which are optionally substituted.

2. Process for the preparation of substituted uracils of the general formula (Ia)

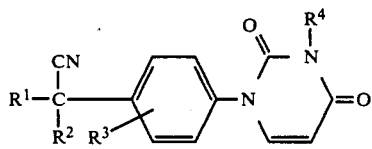

in which $R^1$ represents aromatic or heteroaromatic radicals, which are optionally substituted, $R^2$ represents hydrogen, alkyl, alkenyl, alkinyl or aralkyl, which are optionally substituted, $R^3$ represents one or more identical or different radicals from the group comprising hydrogen, halogen, alkyl, halogenoalkyl, alkoxy, alkylthio, halogenoalkoxy, halogenoalkylthio, cyano, alkoxycarbonyl, alkylsulphonyl and halogenoalkylsulphonyl, $R^4$ represents hydrogen, a straight-chain, branched or cyclic alkyl radical, alkenyl, alkinyl or aralkyl, which are optionally substituted, by (a) heating compounds of the formula (II)

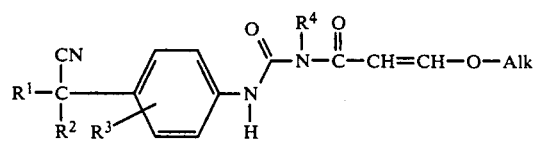

in which $R^1$, $R^2$, $R^3$ and $R^4$ have the abovementioned meanings and Alk represents $C_1$-$C_4$-alkyl, in particular ethyl, if appropriate in the presence of bases, or by (b) reacting compounds of the formula (Ia)

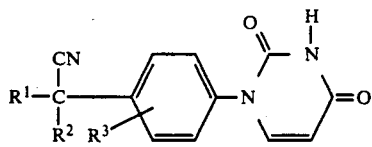

in which $R^1$, $R^2$ and $R^3$ have the abovementioned meanings, with compounds of the formula (III)

$R^4$—A in which $R^4$ represents optionally substituted alkyl, alkenyl, alkinyl or aralkyl and A represents halogen, —$OSO_2$-alkyl, —$OSO_2$-aryl or —$OSO_2$-halogenoalkyl, or by (c) decarboxylating compounds of the formula (IV)

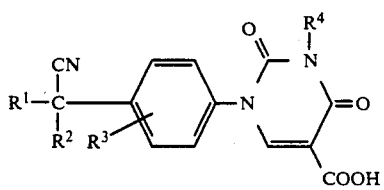

in which $R^1$, $R^2$ and $R^3$ have the abovementioned meanings, by heating.

3. New compounds of the formula (II)

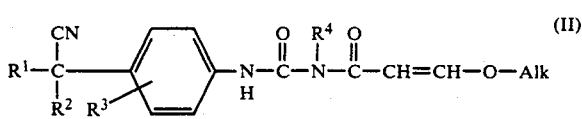

in which $R^1$, $R^2$, $R^3$, $R^4$ and Alk have the meanings indicated in process (2a).

4. Process for the preparation of the compounds of the formula (II) according to 3, characterized in that (a) compounds of the formula (V)

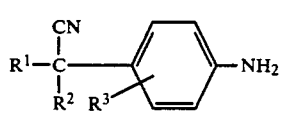

in which $R^1$, $R^2$ and $R^3$ have the abovementioned meanings, are reacted with isocyanates of the formula (VI)

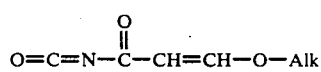

in which Alk has the abovementioned meaning, or (b) compounds of the formula (VII)

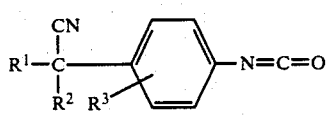

(VII)

in which $R^1$, $R^2$ and $R^3$ have the abovementioned meanings, are reacted with compounds of the formula (VIII)

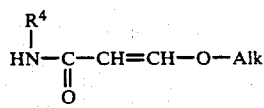

(VIII)

in which $R^4$ or Alk has the abovementioned meanings.

5. New compounds of the formula (VI)

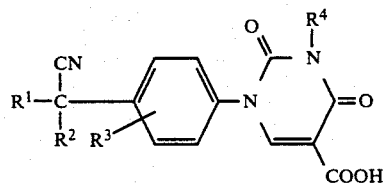

(IV)

in which $R^1$, $R^2$, $R^3$ and $R^4$ have the abovementioned meanings.

6. Process for the preparation of the new compounds of the formula (IV) according to 5, characterized in that compounds of the formula (IX)

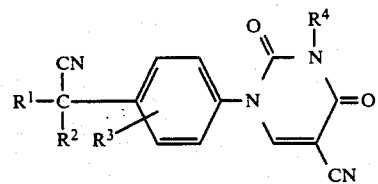

(IX)

in which $R^1$, $R^2$, $R^3$ and $R^4$ have the abovementioned meanings are heated in the presence of the aqueous acids.

7. New compounds of the formula (IX)

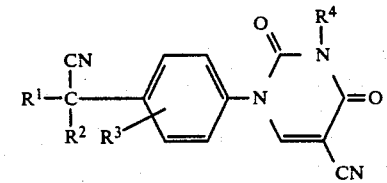

(IX)

in which $R^1$, $R^2$, $R^3$ and $R^4$ have the abovementioned meanings.

8. Process for the preparation of the new compounds of the formula (IX) according to 7., characterized in that compounds of the formula (X)

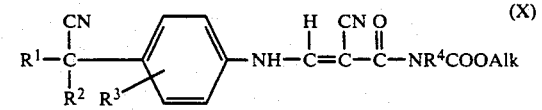

(X)

in which $R^1$, $R^2$, $R^3$, $R^4$ and Alk have the abovementioned meaning, are heated in the presence of bases.

9. New compounds of the formula (X)

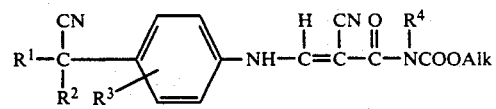

(X)

in which $R^1$, $R^2$, $R^3$, $R^4$ and Alk have the meanings described under 4 (B).

10. Process for the preparation of the new compounds of the formula (X) according to 9., characterized in that compounds of the formula (V)

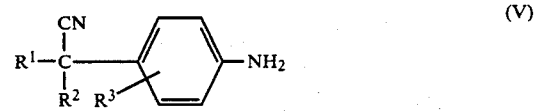

(V)

in which $R^1$, $R^2$ and $R^3$ have the meanings described under 4 (b) are reacted with compounds of the formula (XI)

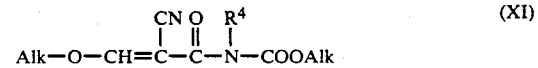

(XI)

in which Alk represents identical or different $C_1$-$C_4$-alkyl.

The compounds of the formula (I) and their salts with acids or bases are outstandingly suitable for combating parasitic protozoa.

Preferred compounds of the formula (I) are compounds in which $R^1$ represents thiazolyl, oxazolyl, benzothiazolyl, benzoxazolyl, pyridinyl, pyrimidinyl, pyrazinyl, indolyl, benzimidazolyl, thienyl, phenyl or naphthyl optionally substituted by halogen, alkyl, cyano, alkoxy, alkylthio, methylenedioxy, ethylenedioxy, alkylsulphinyl, alkylsulphonyl, halogenoalkyl, halogenoalkoxy, halogenoalkylthio, halogenoalkylsulphinyl or halogenoalkylsulphonyl, $R^2$ represents H or alkyl, $R^3$ represents one or more identical or different radicals from the group comprising halogen, alkyl, halogenoalkyl, alkoxy, halogenoalkoxy, alkylthio, halogenoalkylthio or cyano, $R^4$ represents hydrogen, alkyl, alkenyl or alkinyl, which are optionally substituted by halogen, halogenoalkyl, alkoxy, alkylthio, aryloxy, arylthio or aryl.

Particularly preferred compounds of the formula (I) are those in which $R^1$ represents phenyl, pyridyl or benzothiazolyl, each of which is optionally substituted by one or more identical or different radicals from the group comprising halogen, $C_{1-4}$-alkyl, $C_{1-4}$-halogenoalkyl, $C_{1-4}$-alkoxy, $C_{1-4}$-alkylthio, $C_{1-4}$-halogenoalkoxy, $C_{1-4}$-halogenoalkylthio, cyano, $C_{1-4}$-alkoxycarbonyl, $C_{1-4}$-alkylsulphinyl, $C_{1-4}$-alkylsulphonyl, $C_{1-4}$-halogenoalkylsulphinyl and $C_{1-4}$-halogenoalkylsulphonyl, $R^2$ represents H or $C_{1-4}$-alkyl, $R^3$ represents one or more identical or different radicals from the group comprising hydrogen, halogen, $C_{1-4}$-alkyl or $C_{1-4}$-halogenoalkyl and $R^4$ represents hydrogen.

Very particularly preferred compounds of the formula (I) are those in which $R^1$ represents phenyl which is optionally substituted by halogen, in particular chlorine, bromine or fluorine, $C_{1-4}$-halogenoalkyl, in particular trifluoromethyl, $C_{1-4}$-halogenoalkylthio, in particular trifluoromethylthio, $C_{1-4}$-halogenoalkoxy, in particular trifluoromethoxy, $C_{1-4}$-alkyl, in particular methyl, $C_1$-$C_4$-halogenoalkylsulphinyl, such as trifluoromethylsulphinyl, or $C_1$-$C_4$-halogenoalkylsulphonyl, such as trifluoromethylsulphonyl, $R^2$ represents H or $C_{1-4}$-alkyl, in particular methyl, $R^3$ represents halogen, in particular bromine, chlorine or fluorine, $C_{1-4}$-alkyl, in particular methyl, or halogenoalkyl, in particular trifluoromethyl and $R^4$ represents hydrogen.

Individual compounds which may be mentioned are:

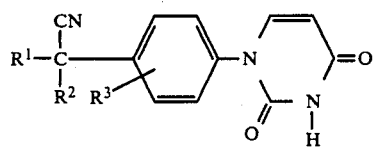

| $R^1$ | $R^2$ | $R^3$ |
|---|---|---|
| 4-Cl-Phenyl | H | 3,5 $Cl_2$ |
| 4-$SCF_3$-Phenyl | H | 3,5 $Cl_2$ |
| 4-$OCF_3$-Phenyl | H | 3,5 $Cl_2$ |
| 4-$SOCF_3$-Phenyl | H | 3,5 $Cl_2$ |
| 4-$SO_2CF_3$-Phenyl | H | 3,5 $Cl_2$ |
| 4-$CF_3$-Phenyl | H | 3,5 $Cl_2$ |
| 3-Cl-4$CF_3$-Phenyl | H | 3,5 $Cl_2$ |
| 3,4-$Cl_2$-Phenyl | H | 3,5 $Cl_2$ |

The following compounds may furthermore be mentioned:

| $R^1$ | $R^2$ | $R^3$ | $R^4$ |
|---|---|---|---|
| 2-Benzthiazolyl | H | 3-Cl | H |
| 2-Benzthiazolyl | H | 3,5-$Cl_2$ | H |
| 2-(6-Cl-Benzthiazolyl) | H | 3-Cl | H |
| 2-(6-Cl-Benzthiazolyl) | H | 3,5-$Cl_2$ | H |
| 2-(5,6-Cl-Benzthiazolyl) | H | 3-Cl | H |
| 2-(5,6-Cl-Benzthiazolyl) | H | 3,5-$Cl_2$ | H |
| 2-Benzoxazolyl | H | 3-Cl | H |
| 2-Benzoxazolyl | H | 3,5-$Cl_2$ | H |
| 2-Pyridinyl | H | 3-Cl | H |
| 3-Pyridinyl | H | 3,5-$Cl_2$ | H |
| 4-Cl Phenyl | H | 3-$CH_3$ | H |
| 4-Cl Phenyl | H | 3-Cl | H |
| 4-Cl Phenyl | H | 3-Cl, 5-$CH_3$ | H |
| 4-Cl Phenyl | H | 3,5-$Br_2$ | H |
| 4-Cl Phenyl | H | 3-$CF_3$ | H |
| 4-$CF_3$ Phenyl | H | 3-$CH_3$ | H |
| 4-$CF_3$ Phenyl | H | 3-Cl | H |
| 4-$CF_3$ Phenyl | H | 3-Cl, 5-$CH_3$ | H |
| 4-$CF_3$ Phenyl | H | 3,5-$Br_2$ | H |
| 4-$CF_3$ Phenyl | H | 3-$CF_3$ | H |
| 4-F-Phenyl | H | 3,5-$Cl_2$ | H |
| 3,4-$Cl_2$-Phenyl | H | 3-$CH_3$ | H |
| 3,4-$Cl_2$-Phenyl | H | 3-Cl | H |
| 3,4-$Cl_2$-Phenyl | H | 3-Cl, 5-$CH_3$ | H |
| 3,4-$Cl_2$-Phenyl | H | 3,5-$Br_2$ | H |
| 3,4-$Cl_2$-Phenyl | H | 3-$CF_3$ | H |
| 3,4-$Cl_2$-Phenyl | H | 3-$CH_3$ | H |
| 2,4-$Cl_2$-Phenyl | H | 3-$CH_3$ | H |
| 2,4-$Cl_2$-Phenyl | H | 3-Cl | H |
| 2,4-$Cl_2$-Phenyl | H | 3-Cl, 5-$CH_3$ | H |
| 2,4-$Cl_2$-Phenyl | H | 3,5-$Br_2$ | H |
| 2,4-$Cl_2$-Phenyl | H | 3-$CF_3$ | H |
| 3-Cl-Phenyl | H | 3-$CH_3$ | H |
| 3-Cl-Phenyl | H | 3-Cl | H |
| 3-Cl-Phenyl | H | 3-Cl, 5-$CH_3$ | H |
| 3-Cl-Phenyl | H | 3,5-$Br_2$ | H |
| 3-Cl-Phenyl | H | 3-$CF_3$ | H |
| 4-$SCF_3$-Phenyl | H | 3-$CH_3$ | H |
| 4-$SCF_3$-Phenyl | H | 3-Cl | H |
| 4-$SCF_3$-Phenyl | H | 3-Cl, 5-$CH_3$ | H |
| 4-$SCF_3$-Phenyl | H | 3,5-Br | H |
| 4-$SCF_3$-Phenyl | H | 3-$CF_3$ | H |
| 4-$SCF_3$-Phenyl | H | 3-$CH_3$ | H |
| 4-$OCF_3$-Phenyl | H | 3-$CH_3$ | H |
| 4-$SCF_3$-Phenyl | $CH_3$ | 3,5-$Cl_2$ | H |
| 4-$OCF_3$-Phenyl | $CH_3$ | 3,5-$Cl_2$ | H |
| 4-$OCF_3$-Phenyl | H | 3-Cl | H |
| 4-$OCF_3$-Phenyl | H | 3-Cl, 5-$CH_3$ | H |
| 4-$OCF_3$-Phenyl | H | 3,5-$Br_2$ | H |
| 4-$OCF_3$-Phenyl | H | 3-$CF_3$ | H |
| 4-CN-Phenyl | H | 3-$CH_3$ | H |
| 4-CN-Phenyl | H | 3-Cl | H |
| 4-CN-Phenyl | H | 3-Cl, 5-$CH_3$ | H |
| 4-CN-Phenyl | H | 3,5-$Br_2$ | H |
| 4-CN-Phenyl | H | 3-$CF_3$ | H |
| 4-$OCH_3$-Phenyl | H | 3-$CH_3$ | H |
| 4-$OCH_3$-Phenyl | H | 3-Cl | H |
| 4-$OCH_3$-Phenyl | H | 3-Cl, 5-$CH_3$ | H |
| 4-$OCH_3$-Phenyl | H | 3,5-$Br_2$ | H |
| 4-$OCH_3$-Phenyl | H | 3-$CF_3$ | H |
| 4-$SO_2CF_3$-Phenyl | H | 3-$CH_3$ | H |
| 4-$SO_2CF_3$-Phenyl | H | 3-Cl | H |
| 4-$SO_2CF_3$-Phenyl | H | 3-Cl, 5-$CH_3$ | H |
| 4-$SO_2CF_3$-Phenyl | H | 3,5-$Br_2$ | H |
| 4-$SO_2CF_3$-Phenyl | H | 3-$CF_3$ | H |
| 4-$SOCF_3$-Phenyl | H | 3-$CH_3$ | H |
| 4-$SOCF_3$-Phenyl | H | 3-Cl | H |
| 4-$SOCF_3$-Phenyl | H | 3-Cl, 5-$CH_3$ | H |
| 4-$SOCF_3$-Phenyl | H | 3,5-$Br_2$ | H |
| 4-$SOCF_3$-Phenyl | H | 3-$CF_3$ | H |
| 2-Benzimidazolly | H | 3-Cl | H |
| 2-Indolyl | H | 3-Cl | H |

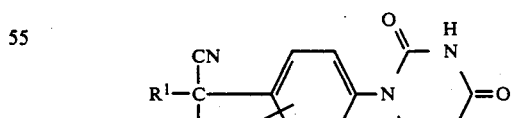

| | | | |
|---|---|---|---|
| 2-Thienyl | H | 3,5-$Cl_2$ | H |
| 4-$SCF_3$-Phenyl | $CH_3$ | 3,5-$Cl_2$ | $CH_3$ |
| 4-Cl-Phenyl | $CH_3$ | 3,5-$Cl_2$ | $CH_3$ |

If 2,6-dichloro-α-(4'-chlorophenyl)-4-(3-ethoxyacryloyl)-ureido-phenylacetonitrile is employed as the compound of the formula (II) in process (2a), the process can be described by the following equation:

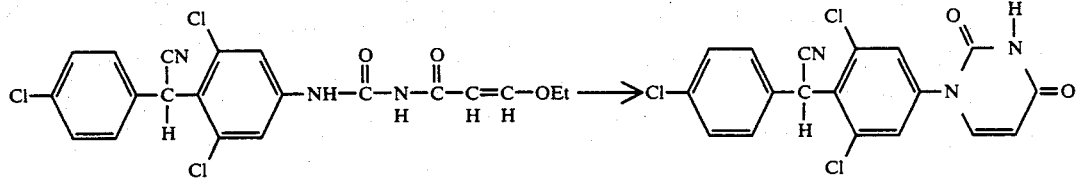

The compounds of the formula (II) are new. They are obtainable by the process described under 4.

Compounds of the formula (II) may be mentioned as preferred in which $R^1$, $R^2$ and $R^3$ have the meanings mentioned as preferred in the compounds of the formula (I).

In particular, the following compounds of the formula (II) may be mentioned:

| $R^1-\overset{CN}{\underset{R^2}{\overset{|}{C}}}-\underset{R^3}{\phantom{M}}\text{—NH—}\overset{O}{\overset{\|}{C}}\text{—NHCO—C=C—CO}_2\text{Et}$ | | |
|---|---|---|
| $R^1$ | $R^2$ | $R^3$ |
| Cl—⌬— | H | 3,5-Cl$_2$ |
| Cl—⌬— | H | 3-Cl |
| F$_3$CS—⌬— | H | 3,5-Cl$_2$ |
| F$_3$CO—⌬— | H | 3,5-Cl$_2$ |
| F$_3$C—⌬— | H | 3,5-Cl$_2$ |
| F$_3$CO$_2$S—⌬— | H | 3,5-Cl$_2$ |

Process 2(a) is carried out by heating a compound of the formula (II) in substance or in solution, if appropriate in the form of its salts. After the reaction has ended, the reaction mixture is acidified using dilute inorganic acid (for example hydrochloric acid) and the precipitated solid is filtered off.

Possible diluents here are virtually all inert organic solvents. These preferably include aliphatic and aromatic, optionally halogenated hydrocarbons, benzine, ligroin, benzene, toluene, xylene, methylene chloride, ethylene chloride, carbon tetrachloride, chlorobenzene and o-dichlorobenzene, ethers such as diethyl ether and dibutyl ether, glycol dimethyl ether and diglycol dimethyl ethyl, tetrahydrofuran and dioxane, ketones such as acetone, methyl ketone, ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone and also dimethyl sulphoxide, tetramethyleneic sulphone and hexamethylphosphortriamide, and alcohols such as ethanol or tert. butanol.

The reaction is carried out in the presence of inorganic or organic bases.

Those which may be mentioned are, for example: alkali metal hydroxides such as, for example, sodium hydroxide and potassium hydroxide, alkaline earth metal alkali metal acetates such as sodium acetate, alkali metal carbonates and alkoxides such as sodium carbonate and potassium carbonate, sodium methoxide and potassium methoxide or sodium ethoxide and potassium ethoxide or potassium tert. butoxide, and in addition aliphatic, aromatic or heterocyclic amines, for example triethylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO).

The reaction is carried out at temperatures between 80° C. and 200° C., preferably between 80° C. and 160° C., at normal pressure or elevated pressure. It is preferably carried out at normal pressure.

If 2,6-dichloro-α-(2',4'-dichlorophenyl)-α-methyl-4-(1-uracil)-phenylacetonitrile is employed as the compounds of the formula (Ia) and methyl iodide as the compound of the formula (III) in process (2b), the process can be described by the following equation:

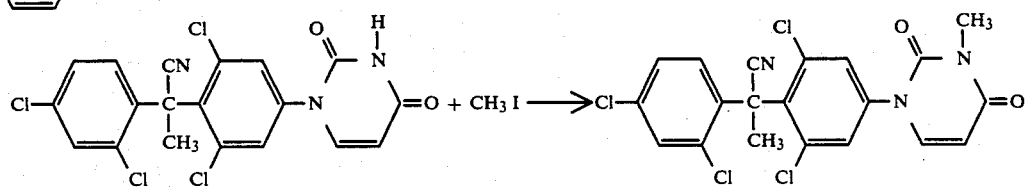

The compounds of the formula (Ia) are new and are prepared as described in process (2a).

The compounds of the formula (IV) are known or can be prepared by known methods. Methyl iodide and ethyl bromide may be particularly mentioned.

The process is carried out by reacting a compound of the formula (Ia) with compounds of the formula (IV) in the presence of a base and a diluent. Diluents employed can be all inert organic diluents which are also used for carrying out process (2a).

The process is carried out in the presence of bases. Preferred bases which may be mentioned are the alkali metal hydroxides such as sodium hydroxide, alkali metal alkoxides such as sodium methoxide or potassium butoxide, metal hydrides such as sodium hydride or organic bases such as 1,8-diazabicyclo[5-undec-7-ene (DBU).

The process is carried out at normal pressure and temperatures between 20° C. and 140° C.

The reaction is carried out by combining equimolar amounts of the compound of the formula (Ia) and base, adding an equimolar amount of the compound of the formula (IV) to this mixture and heating to the reaction temperature.

If 2,6-dichloro-α-(2′,4′-dichlorophenyl)-4-(5-carboxy-1-uracil)-phenylacetonitrile is employed as the compound of the formula (IV) in process (2c) for the preparation of the compounds (I), the process can be described by the following equation:

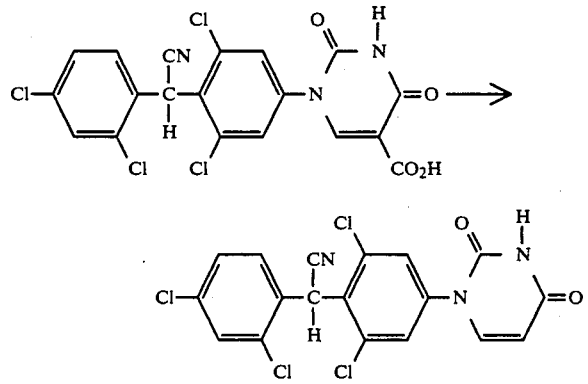

The compounds of the formula (IV) are new. Their preparation is carried out by the process described under (6).

Compounds of the formula (IV) are preferably employed in which $R^1$, $R^2$ and $R^3$ have the preferred and particularly preferred meanings mentioned for the compounds of the formula (I).

Decarboxylation is carried out by heating in the presence of mercapto group-containing carboxylic acids such as, for example, mercaptoacetic acid or thiosalicylic acid, if appropriate in the presence of inert organic diluents. The diluents include aliphatic and aromatic, optionally halogenated hydrocarbons such as nonane, decane, dodecane, xylenes, ethers such as ethylene glycol monobutyl ether and diethylene glycol dibutyl ether.

The reaction is carried out at temperatures between 150° C. and 300° C., preferably between 160° C. and 250° C., in particular 170° C. and 210° C.

The reaction is carried out at normal pressure. The compounds of the formula (IV) are heated, in substance or dissolved or suspended in the particular diluent, together with the mercapto group-containing carboxylic acid.

If 2,6-dichloro-α-(4′-chlorophenyl)-4-aminophenylacetonitrile is employed as the compound of the formula (V) and ethoxyacryloyl isocyanate is employed as the compound of the formula (VI) in process 4 for the preparation of the compounds of the formula (II), the process can be described by the following equation:

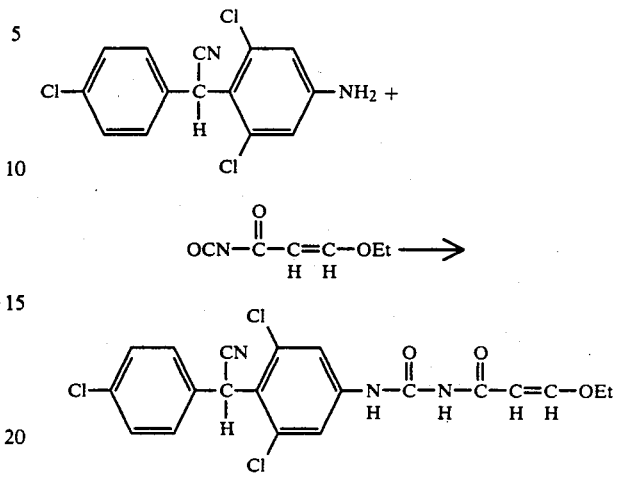

The compounds of the formula (V) are known in some cases (U.S. Pat. No. 4,005,218) or can be prepared by the process described there. In some cases, they are the subject of an as yet unpublished application by the applicant (DE Application 3,834,272.3)

Compounds of the formula (V) may preferably be mentioned in which $R^1$, $R^2$ and $R^3$ have the meanings mentioned in which $R^1$, $R^2$ and $R^3$ have the meanings mentioned as preferred or particularly preferred in the compounds of the formula (I). In particular, the compounds of the following formula may be mentioned:

$$R^1-\underset{\underset{H}{|}}{\overset{\overset{CN}{|}}{C}}-\text{C}_6\text{H}_3(R^3)-NH_2$$

| $R^1$ | $R^3$ |
|---|---|
| 2-(6-chlorobenzothiazolyl) | 3,5-$Cl_2$ |
| 2-benzothiazolyl | 3-Cl |
| 2-benzothiazolyl | 3-$CH_3$ |
| 2-benzothiazolyl | 3,5-$Cl_2$ |
| 2-benzimidazolyl | 3-Cl |
| 2-indolyl | 3-Cl |
| 2-pyridinyl | 3,5-$Cl_2$ |
| 3-pyridinyl | 3,5-$Cl_2$ |
| 4-Cl-phenyl | 3-Cl |
| 4-Cl-phenyl | 3,5-$Cl_2$ |
| 3,4-dichlorophenyl | 3,5-$Cl_2$ |
| $H_3CSO_2$-phenyl | 3,5-$Cl_2$ |

The compounds of the formula (VI) are known.

The reaction is preferably carried out using diluents. Possible diluents here are virtually all inert organic solvents. These preferably include aliphatic and aromatic, optionally halogenated hydrocarbons, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, dimethylacetamide and N-methyl-pyrrolidone and also dimethyl sulphoxide, tetramethyleneic sulphone and hexamethylphosphortriamide.

The reaction is carried out at temperatures between 20° C. and 180° C., preferably between 30° C. and 50° C.

The process is carried out by combining and heating approximately equimolar amounts of the compounds of the formula (V) and (VI) in one of the diluents indicated. After the reaction is complete, the mixture is cooled and the precipitated solid is filtered off, washed and dried.

If 4-isocyanato-2,6-dichloro-α-(4-chlorophenyl)-α-methyl-phenylacetonitrile is employed as the compound of the formula (VII) and N-methylethoxyacrylamide as the compound of the formula (VIII) in process (4b) for the preparation of the compounds of the formula (II), the process can be described by the following equation:

the compound (IV), the process can be described by the following equation:

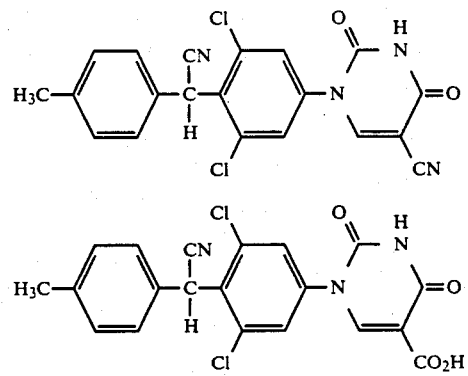

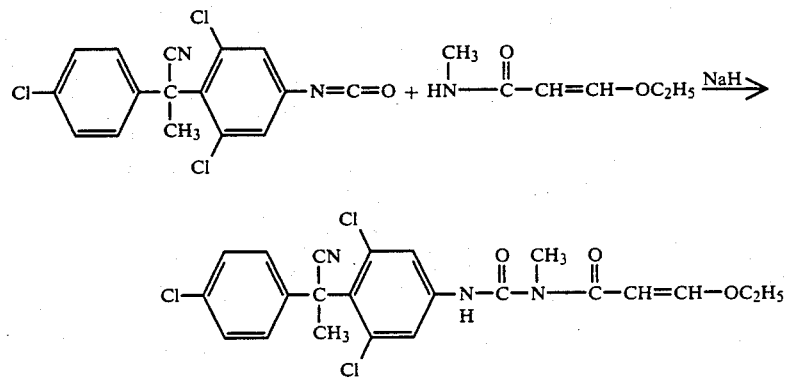

Individual compounds of the formula (VII) which may be mentioned are:

| $R^1$ | $R^2$ | $R^3$ |
|---|---|---|
| benzothiazolyl | H | 3,5-$Cl_2$ |
| 4-Cl-phenyl | H | 3-Cl |
| 4-Cl-phenyl | H | 3,5-$Cl_2$ |
| 4-$OCF_3$-phenyl | H | 3-$CH_3$ |
| 4-$OCF_3$-phenyl | H | 3,5-$Cl_2$ |

The process is carried out by heating approximately equimolar amounts of the compound of the formula (VII) and the compound of the formula (VIII), if appropriate in the presence of a diluent and a base. Diluents used are the solvents mentioned in the preparation of the compounds (I). Pyridine may be additionally mentioned. Bases used are those described in process 2b. Sodium hydride may be mentioned as particularly preferred.

The reaction is carried out under normal or elevated pressure at temperatures between 20° C. and 150° C., preferably between 30° C. and 80° C.

The compounds are preferably employed in equimolar proportions and the product obtained as a solid after the reaction has ended is filtered off.

If 2,6-dichloro-α-(4'-methylphenyl)-4-(5-cyano-2-uracil)phenylacetonitrile is employed as the compound of the formula (IX) in process (6) for the preparation of The compounds of the formula (IX) are new. Their preparation is carried out by the process described under (8). In particular, the following compounds of the formula (IX) may be mentioned:

| $R^1$ | $R^3$ |
|---|---|
| 4-Cl-phenyl | 3,5-$Cl_2$ |
| 4-Cl-phenyl | 3-Cl |
| 4-$CF_3$-phenyl | 3,5-$Cl_2$ |
| 4-$SO_2CF_3$-phenyl | 3,5-$Cl_2$ |
| 4-$CF_3$-phenyl | 3,5-$Cl_2$ |
| 4-$OCF_3$-phenyl | 3,5-$Cl_2$ |
| 2-pyridyl | 3,5-$Cl_2$ |
| 3,4-$Cl_2$-phenyl | 3,5-$Cl_2$ |
| 4-$SCF_3$-phenyl | 3-Cl |
| 4-$OCF_3$-phenyl | 3-Cl |
| 4-$CH_3$-phenyl | 3-Cl |
| 2-benzothiazolyl | 3,5-$Cl_2$ |
| 4-$SO_2CH_3$-phenyl | 3,5-$Cl_2$ |

The hydrolysis is carried out under acidic conditions. Acids used are mineral acids, such as, for example, hydrochloric acid, hydrobromic acid, sulphuric acid and mixtures of mineral acids and organic acids, such as, for example, acetic acid or propionic acid.

The reaction is carried out at temperatures between 80° C. and 120° C. It is carried out under normal pressure.

The compounds of the formula (IX) are dissolved in a 10- to 30-fold volume of the acid or the acid mixture and heated until hydrolysis has ended.

In one variant, the compounds of the formula (I) can be obtained directly starting from the compounds of the formula (IX). This is achieved by addition to the hydrolysis medium of mercapto group-containing carboxylic acids described in process (2c), preferably mercaptoacetic acid.

If 2,6-dichloro-α-(4'-methylphenyl)-4-N-(2-cyanoacryloylurethane)aminophenylacetonitrile is employed as the compound of the formula (X) in process (8) for the preparation of the compounds (IX), the process can be described by the following equation:

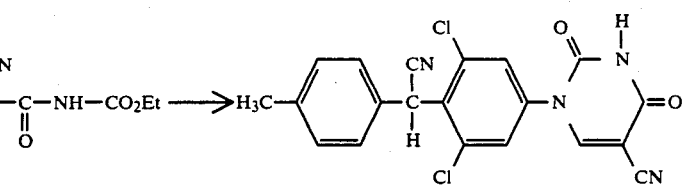

The compounds of the formula X are new. The compounds of the formula X may be mentioned as preferred in which $R^1$, $R^2$ and $R^3$ have the meanings mentioned as preferred in the compounds of the formula I.

In particular, the following compounds of the formula SX may be mentioned:

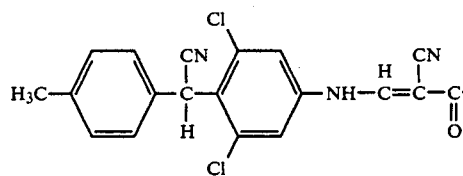

| $R^1$ | $R^3$ |
|---|---|
| 4-Cl-phenyl | 3,5-Cl$_2$ |
| 4-Cl-phenyl | 3-Cl |
| 4-FCS-phenyl | 3,5-Cl$_2$ |
| 4-F$_3$CSO$_2$-phenyl | 3,5-Cl$_2$ |
| 4-OCF$_3$-phenyl | 3,5-Cl$_2$ |
| 4-CF$_3$-phenyl | 3,5-Cl$_2$ |
| 2-pyridyl | 3,5-Cl$_2$ |
| 3,4-Cl$_2$-phenyl | 3,5-Cl$_2$ |
| 3,4-Cl$_2$-phenyl | 3,5-Cl$_2$ |
| 4-CF$_3$, 3-Cl-phenyl | 3-Cl |
| 4-SCF$_3$-phenyl | 3-Cl |
| 4-CH$_3$-phenyl | 3-Cl |
| 4-OCF$_3$-phenyl | 3-Cl |
| 2-benzothiazolyl | 3,5-Cl$_2$ |
| 4-SO$_2$CH$_3$-phenyl | 3,5-Cl$_2$ |

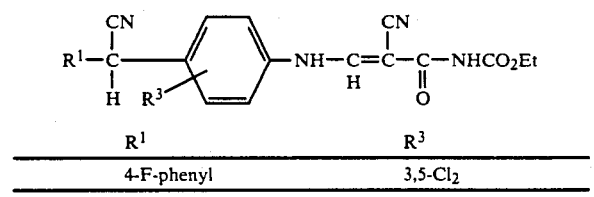

| $R^1$ | $R^3$ |
|---|---|
| 4-F-phenyl | 3,5-Cl$_2$ |

The process is carried out by heating a compound of the formula (X), if appropriate in the presence of a solvent and a base.

Solvents mentioned in the preparation of the compounds (I) are used as solvents and bases. Particularly preferred organic solvents which are employed are alcohols such as, for example, ethanol or organic acids such as, for example, glacial acetic acid.

Particularly preferred bass are the hydroxides and acetates of the alkali metals or alkaline earth metals such as, for example, NaOH or sodium and potassium acetate.

The reaction is carried out under normal pressure at temperatures between 70° C. and 150° C., preferably between 70° C. and 100° C.

The base used is employed in a 10 to 80% strength molar excess. The reaction mixture is acidified after cyclization has ended, preferably using a dilute mineral acid such as, for example, hydrochloric acid and the product obtained as a solid is filtered off.

If 2,6-dichloro-α-(4'-methylphenyl)-4-aminophenylacetonitrile and N-(2-cyano-3-ethoxyacryloyl-)urethane is employed as the compound of the formula (XI) in process (10) for the preparation of the compounds (X), the process can be described by the following equation:

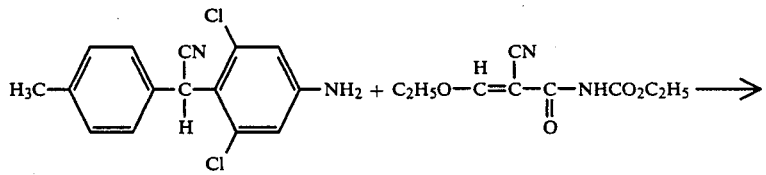

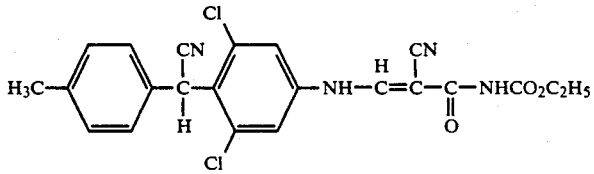

The process is carried out by heating compounds of the formula (V) with an approximately equimolar amount of N-(2-cyano-3-alkoxy-acryloyl)urethane in a diluent and filtering off the solid obtained after cooling with suction.

Possible solvents are those mentioned in process (2a).

The reaction is carried out between 50° C. and 150° C., preferably between 80° C. and 100° C.

The active compounds are suitable for combating parasitic protozoa which are encountered and in the keeping and raising of animals with productive, breeding, zoo, laboratory, experimental and pet animals, and have favourable toxicity to warm-blooded animals. They are active against all or individual stages of development of the pests and against resistant and normally sensitive strains. By combating the parasitic protozoa, disease, cases of death and yield reductions (for example in the production of meat, milk, wool, hides, eggs, honey etc.) should be reduced so that more economical and simpler keeping of animals is possible through the use of the active compounds.

The parasitic protozoa include:

Mastigophora (Flagellata) such as, for example, Trypanosomatidae, for example *Trypanosoma b. brucei, T.b. gambiense, T.b. rhodesiense, T. congolense, T. cruzi, T. evansi, T. equinum, T. lewisi, T. percae, T. simiae, T. vivax, Leishmania brasiliensis, L. donovani, L. tropica,* such as, for example, Trichomonadidae, for example *Giardia lamblia* and *G. canis.*

Sarcomastigophora (Rhizopoda) such as Entamoebidae, for example *Entamoeba histolytica,* Hartmanellidae, for example Acanthamoeba sp. and Hartmanella sp.

Apicomplexa (Sporozoa) such as Eimeridaj, for example *Eimeria acervulina, E. adenoides, E. alabahmensis, E. anatis, E. anseris, E. arloingi, E. ashata, E. auburnensis, E. bovis, E. brunetti, E. canis, E. chinchillae, E. clupearum, E. columbae, E. contorta, E. crandalis, E. dabliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E. ninakohlyakimovae, E. ovis, E. parva, E. pavonis, E. perforans, E. phasani, E. piriformis, E. praecox, E. residua, E. scabra, E. spec., E. steidai, E. suis, E. enella, E. truncata, E. truttae, E. zuernii, Globidium spec., Isospora belli, I. canis, I. felis, I. ohioensis, I. rivolta, I. spec., I. suis, Cystisospora spec., Cryptosporidium spec.* such as Toxoplasmadidae, for example *Toxoplasma gondii,* such as Sarcocystidae, for example *Sarcocystis bovicanis, S. bovihominis, S. ovicanis, S. ovifelis, S. spec., S. suihominis* such as Leucozoidae, for example *Leucozytozoon simondi,* such as Plasmodiidae, for example *Plasmodium berghei, P. falciparum, P. malariae, P. ovale, P. vivax, P. spec.,* such as Piroplasmea, for example *Babesia argentina, B. bovis, B. canis,* B. spec., *Theileria parva,* Theileria spec., such as Adeleina, for example *Hepatozoon canis,* H. spec.

In addition *Pneumocystis carinii* and Ciliophora (Ciliata) such as, for example, *Balantidium coli,* Ichthiophthirius spec., Trichodina spec. and Epistylis spec.

The compounds according to the invention are moreover active against various fish parasites which belong to the helminths (worms).

The productive and breeding animals include mammals such as, for example, cattle, horses, sheep, pigs, goats, camels, water buffalo, donkeys, rabbits, fallow deer, reindeer, animals having a valuable coat such as, for example, mink, chinchilla, racoons, birds such as, for example, hens, geese, turkeys, ducks, doves, and species of bird for keeping at home and in the zoo. In addition, productive and ornamental fish are included.

The laboratory and experimental animals include mice, rats, guinea pigs, golden hamsters, dogs and cats.

The pet animals include dogs and cats.

The fish include productive, breeding, aquarium and ornamental fish of all ages which live in fresh and salt water. The productive and breeding fish include, for example, carp, eel, trout, white fish, salmon, bream, roach, rud, chub, sole, plaice, halibut, Japanese yellowtail (*Seriola quinqueradiata*), Japanese eel (*Anguilla japonica*), red seabream (*Pagurus major*), sea bass (*Dicentrarchus labrax*), grey mullet (*Mugilus cephalus*), pompano, gilthread seabream (*Sparus auratus*), Tilapia spp., chichlidae species such as, for example, Plagioscion or Channel catfish. The agents according to the invention are particularly suitable for the treatment of fry, for example carp of 2–4 cm body length. The agents are also very highly suitable in the feeding of eels.

Administration can be carried out both prophylactically and therapeutically.

The administration of the active compounds is carried out directly or enterally, parenterally, dermally or nasally in the form of suitable preparations.

Enteral administration of the active compounds is carried out, for example, orally in the form of powders, suppositories, tablets, capsules, pastes, drinks, granules, drenches, boli, medicated feed or drinking water. Dermal administration can be carried out, for example, in the form of dipping, spraying, bathing, washing, pouring-on and spotting-on and powdering. Parenteral administration is carried out, for example, in the form of the injection (intramuscular, subcutaneous, intravenous, intraperitoneal) or by implants.

Suitable preparations are: solutions such as injection solutions, oral solutions, concentrates for oral administration after dilution, solutions for use on the skin or in body cavities, pouring-on formulations and gels; emulsions and suspensions for oral or dermal administration and also for injection; semi-solid preparations; formulations in which the active compound is processed in an ointment base or in an oil-in-water or water-in-oil emulsion base; solid preparations such as powders, premixes or concentrates, granules, pellets, tablets, boli, capsules; aerosols and inhalants, and molded articles containing active compound.

Injection solutions are administered intravenously, intramuscularly and subcutaneously.

Injection solutions are produced by dissolving the active compound in a suitable solvent and, if necessary, adding additives such as solubilizers, acids, bases, buffer salts, antioxidants and preservatives The solutions are sterile filtered and bottled.

Solvents which may be mentioned are: physiologically tolerable solvents such as water, alcohols such as ethanol, butanol, benzyl alcohol, glycerol, hydrocarbons, propylene glycol, polyethylene glycols, N-methylpyrrolidone, and mixtures of these.

The active compounds may optionally also be dissolved in physiologically tolerable vegetable or synthetic oils which are suitable for injection.

Solubilizers which may be mentioned are: solvents which promote the solution of the active compound in the main solvent or prevent its precipitation. Examples are polyvinylpyrrolidone, polyoxyethylated castor oil and polyoxyethylated sorbitan esters.

Preservatives are: benzyl alcohol, trichlorobutanol, p-hydroxybenzoic acid esters and n-butanol.

Oral solutions are administered directly. Concentrates are administered orally after previously diluting to the administration concentration. Oral solutions and concentrates are prepared as described above for the injection solutions, it being possible to dispense with sterile working.

Solutions for use on the skin are poured on dropwise, spread on, rubbed in, sprinkled on, sprayed on or applied by dipping, bathing or washing. These solutions are prepared as described above for the injection solutions.

It may be advantageous to add thickeners during the preparation. Thickeners are: inorganic thickeners such as bentonites, colloidal silica, aluminum monostearate, organic thickeners such as cellulose derivatives, polyvinyl alcohols and their copolymers, acrylates and metacrylates.

Gels are applied to or spread on the skin or introduced into body cavities. Gels are prepared by adding such a quantity of thickener to solutions which have been prepared as described for the injection solutions that a clear composition having an ointment-like consistency results. The thickeners indicated above are employed as thickeners.

Pouring-on formulations are poured onto or sprinkled onto limited areas of the skin, whereupon the active compound either penetrates the skin and acts systemically or is distributed on the body surface Pouring-on formulations are prepared by dissolving, suspending or emulsifying the active compound in suitable skin-compatible solvents or solvent mixtures. If appropriate, further auxiliaries such as colorants, absorption-promoting substances, antioxidants, light screens and adhesives are added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetates, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, aromatic and/or aliphatic hydrocarbons, vegetable or synthetic oils, DMF, dimethylacetamide, N-methylpyrrolidone and 2-dimethyl-4-oxy-methylene-1,3-dioxolane.

Colorants are all colorants which may be dissolved or suspended and which are permitted for administration to animals.

Absorption-promoting substances are, for example, DMSO, spreading oils such as isopropyl myristate, dipropylene glycol pelargonate, silicone oils, fatty acid esters, triglycerides and fatty alcohols.

Antioxidants are sulphites or metabisulphites such as potassium metabisulphite, ascorbic acid, butylhydroxytoluene, butylhydroxyanisole and tocopherol.

Light screens are, for example, substances of the benzophenone class or novantisolic acid.

Adhesives are, for example, cellulose derivatives, starch derivatives, polyacrylates, and natural polymers such as alginates and gelatin.

Emulsions may be administered orally, dermally or as injections.

Emulsions are either of the water-in-oil type or the oil-in-water type.

They are prepared by dissolving the active compound either in the hydrophobic or the hydrophilic phase and homogenizing this with the solvent of the other phase with the aid of suitable emulsifiers and, if appropriate, further auxiliaries such as colorants, absorption-promoting substances, preservatives, antioxidants, light screens and viscosity-increasing substances.

Hydrophobic phases (oils) which may be mentioned are: paraffin oils, silicone oils, natural vegetable oils such as sesame oil, almond oil, castor oil, synthetic triglycerides such as caprylic/capric acid biglyceride, triglyceride mixture with vegetable fatty acids of chain length $C_{8-12}$ or other specially selected natural fatty acids, partial glyceride mixtures of saturated or unsaturated fatty acids possibly also containing hydroxyl groups, and mono- and diglycerides of $C_8/C_{10}$-fatty acids.

Fatty acid esters such as ethyl stearate, di-n-butyryl adipate, hexyl laurate, dipropylene glycol pelargonate, esters of a branched fatty acid of medium chain length containing saturated fatty alcohols of chain length $C_{16}$–$C_{18}$, isopropyl myristate, isopropyl palmitate, caprylic/capric acid esters of saturated fatty alcohols of chain length $C_{12}$–$C_{18}$, isopropyl stearate, oleyl oleate, decyl oleate, ethyl oleate, ethyl lactate, waxy fatty acid esters such as dibutyl phthalate, diisopropyl adipate, ester mixtures related to the latter, inter alia fatty alcohols such as isotridecyl alcohol, 2-octyldodecanol, cetyl stearyl alcohol and oleyl alcohol.

Fatty acids such as, for example, oleic acid and its mixtures.

Hydrophilic phases which may be mentioned are: water, alcohols such as, for example, propylene glycol, glycerol, sorbitol and their mixtures.

Emulsifiers which may be mentioned are: non-ionic surfactants, for example polyoxyethylated castor oil, polyoxyethylated sorbitan monooleate, sorbitan monostearate, glycerol monostearate, polyoxyethyl stearate and alkylphenol polyglycol ethers; ampholytic surfactants such as di-Na N-lauryl-$\beta$-imino-dipropionate or lecithin; anionic surfactants, such as Na lauryl sulphate, fatty alcohol ether sulphates, mono/dialkyl polyglycol ether orthophosphoric acid ester monoethanolamine salt; cationic surfactants such as cetyltrimethylammonium chloride.

Other auxiliaries which may be mentioned are: substances increasing viscosity and stabilizing the emulsion such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silica or mixtures of the substances mentioned.

Suspensions may be administered orally, dermally or as an injection. They are prepared by suspending the active compound in an excipient liquid, if appropriate with the addition of other auxiliaries such as wetting agents, colorants, absorption-promoting substances, preservatives, antioxidants light screens.

Excipient liquids which may be mentioned are all homogeneous solvents and solvent mixtures.

Wetting agents (dispersants) which may be mentioned are the surfactants indicated above.

Other auxiliaries which may be mentioned are those indicated above.

Semi-solid preparations can be administered orally or dermally. They differ from the suspensions and emulsions described above only by their higher viscosity.

In order to prepare solid preparations, the active compound is mixed with suitable excipients, if appropriate with the addition of auxiliaries, and brought into the desired form.

Excipients which may be mentioned are all physiologically tolerable solid inert substances. Those used are inorganic and organic substances. Inorganic substances are, for example, sodium chloride, carbonates such as calcium carbonate, hydrogen carbonates, aluminum oxides, silicic acids, aluminas, precipitated or colloidal silica and phosphates.

Organic substances are, for example, sugars, cellulose, foodstuffs and feeds such as milk powder, animal meal, cereal meal and shreds, and starches.

Auxiliaries are preservatives, antioxidants and colorants which have already been mentioned above.

Other suitable auxiliaries are lubricants and glidants such as, for example, magnesium stearate, stearic acid, talc, bentonites, disintegration-promoting substances such as starch or crosslinked polyvinylpyrrolidone, binders such as, for example, starch, gelatin or linear polyvinylpyrrolidone and dry binders such as microcrystalline cellulose.

The active compounds may also be present in the preparations as a mixture with synergists or with other active compounds.

Ready to use preparations contain the active compound in concentrations of 10 ppm -20 percent by weight, preferably from 0.1-10 per cent by weight.

Preparations which are diluted before use contain the active compound in concentrations of 0.5–90 percent by weight, preferably from 1 to 50 percent by weight.

In general, it has proved advantageous administer amounts of about 0.5 to about 50 mg, preferably 1 to 20 mg, of active compound per kg of body weight per day to attain effective results.

The active compounds can also be administered together with the feed or drinking water of the animals.

Feeds and foodstuffs contain 0.01 to 100ppm, preferably 0.5 to 50 ppm of the active compound in combination with a suitable edible material.

Such a feed or foodstuff can be used both for healing purposes and for prophylactic purposes.

The preparation of such a feed or foodstuff is carried out by mixing a concentrate or a premix which contains 0.5 to 30%, preferably 1 to 20% by weight, of an active compound in a mixture with an edible organic or inorganic excipient with customary feeds. Edible excipients are, for example, maize flour or maize and soya bean flour or mineral salts which preferably contain a small amount of an edible dust-preventing oil, for example maize oil or soya oil. The premix obtained in this way can then be added to the complete feed before feeding it to the animals.

Use in coccidiosis may be mentioned as an example:

For the curing and prophylaxis, for example, of coccidiosis in poultry, in particular in hens, ducks, geese and turkeys, 0.1 to 100 ppm, preferably 0.5 to 100 ppm, of an active compound are mixed with a suitable edible material, for example a nutritious feed If desired, these amounts can be increased, particularly if the active compound is well tolerated by the recipient. Administration can correspondingly be carried out via the drinking water.

For the treatment of individual animals, for example in the case of the treatment of coccidiosis in mammals or toxoplasmosis, preferably amounts of active compound of 0.5 to 100 mg/kg of body weight are administered daily in order to obtain the desired results. In spite of this it may be periodically necessary to deviate from the amounts mentioned, in particular depending on the body weight of the test animal or the type of administration method, but also on account of the type of animal and its individual reaction to the active compound or the manner of formulation and the time or the interval at which it is administered. Thus, in certain cases it may be sufficient to manage with less than the minimum amount previously mentioned, whereas in other cases the upper limit mentioned must be exceeded. With the administration of larger amounts, it may be expedient to divide these into a number of individual administrations over the course of the day.

The fish parasites include from the sub-kingdom of the protozoa, species of the Ciliata strain, for example *Ichthyophthirius multifiliis, Chilodonella cyprini,* Trichodina spp., Glossatella spp., Epistylis spp. of the Myxosporidia strain, for example *Myxosoma cerebralis,* Myxidium spp., Myxobolut spp., Henequya spp., Glugea spp., Thelohania spp., Pleistophora spp., from the flat helminths strain: trematodes; Monogenea, for example Dactylogyrus spp., Gyrodactylus spp., Pseudodactylogyrus spp., Diplozoon spp., cestodes, for example from the Caryphyllidea group (for example *Caryophyllaeus laticeps*), Pseudophyllidea (for example Diphyllobothrium spp.), Tetraphyllidea (for example Phyllobothrium spp.) and Protocephalida (for example species of the genus Proteocephalus) and from the strain of the Arthropoda, various parasitic crustaceae, in particular from the subclasses of the Branchiura (fish-lice) and Copepoda (Copepods) and the orders of the Isopoda (isopods) and Amphipoda (amphipods).

The treatment of the fish is carried out either orally, for example via the feed or by short-term treatment, "medicinal bath", into which the fish are put and in which they are kept for some time (minutes up to a number of hours), for example when transferring from one breeding pond to the other.

However, temporary or permanent treatment of the living space of the fish (for example entire pool units, aquaria, tanks or ponds), in which the fish are kept, can also be carried out.

The active compound is administered in preparations which are suited to the applications.

The concentration of the active compound in the preparations is 1 ppm to 10 % by weight.

Preferred preparations for short-term treatment in the course of use as a "medicinal bath", for example in the treatment when transferring the fish or for the treatment of the living space (pool treatment) of the fish, are solutions of the active compound in one or more polar solvents which give an alkaline reaction on diluting with water.

For the preparation of these solutions, the active compound is dissolved in a polar, water-soluble solvent which either gives an alkaline reaction or to which is added an alkaline water-soluble substance. The latter is advantageously also dissolved in the solvent, but can also be suspended in the solvent and only dissolve in the water. After addition of the active compound solution, the water should have a pH of 7-10, but preferably a pH of 8-10.

The concentration of the active compound can be in the range from 0.5–50%, but preferably in a range from 1–25%.

Suitable solvents are all water-soluble solvents in which the active compound is soluble at a sufficient concentration and which are physiologically acceptable.

These are ethyl alcohol, isopropyl alcohol, benzyl alcohol, glycerol, propylene glycol, polyethylene glycols, poly(oxoethylene)-poly(oxypropylene) polymers, basic alcohols such as mono-, di- and triethanolamine, ketones such as acetone or methyl ethyl ketone, esters such as ethyl lactates, in addition N-methylpyrrolidone, dimethylacetamide, dimethylformamide, and in addition dispersants and emulsifiers such as polyoxyethylated castor oil, polyethylene glycol sorbitan monooleate, polyethylene glycol stearate or polyethylene glycol ethers and polyethylene glycol alkylamines.

Bases which may be mentioned for adjusting the alkaline pH are organic bases such as basic amino acids such as L- or D,L-arginine, L- or D,L-lysine, methylglucosamine, glucosamine, 2-amino-2-hydroxymethyl-propane-1,3-diol and in addition such as N,N,N',N'-tetrakis-(2-hydroxypropyl)-ethylenediamine or polyether tetrol based on ethylenediamine (M.W. 480–420), inorganic bases, such as ammonia or sodium carbonate —if appropriate with the addition of water.

The preparations may also contain 0.1 to 20 % by weight, preferably 0.1–10 % by weight, of other formulation auxiliaries, such as antioxidants, surfactants, suspension stabilizers and thickeners such as, for example, methylcellulose, alginates, polysaccharides, galactomannans and colloidal silicic acid. The addition of colorants, flavoring and builders for animal nutrition is also possible. Even acids which, together with the base initially introduced, form a buffer system or reduce the pH of the solution, can be mentioned here.

The concentration of the active compound during use depends on the type and duration of the treatment, and the age and condition of the treated fish. It is, for example, for a short-term treatment, 2–50 mg of active compound per liter of water, preferably 5–10 mg per liter, for a treatment period of 3–4 hours. For the treatment of young carp, for example, a concentration of 5–10 mg/l and a treatment period of about 1–4 hours are used.

Eels are treated using concentrations of about 5 mg/l for about 4 hours.

For a relatively long treatment period or for continuous treatment, the concentration can be chosen to be correspondingly lower.

For pool treatments, 0.1–5 mg of active compound per liter of water can be used.

Preparations for use as a food additive are, for example, composed as follows:

| (a) Active compound of the formula I | 1–10 parts by weight |
|---|---|
| Soya bean protein | 49–90 parts by weight |
| (b) Active compound of the formula I | 0.5–10 parts by weight |
| Benzyl alcohol | 0.08–1.4 parts by weight |
| Hydroxypropyl-methyl cellulose | 0–3.5 parts by weight |
| Water | remainder to 100 |

Preparations for use in "medicinal baths" and for pool treatment are, for example, composed and prepared as follows.

(C) 2.5 g of active compound of the formula (I) are dissolved in 100 ml of triethanolamine with warming.

(d) 2.5 g of active compound of the formula (I), 12.5 g of lactic acid are dissolved in 100 ml of trtiethanolamine with warming and stirring.

(e) 10.0 g of active compound of the formula (I) is dissolved in 100 ml of monoethanolamine.

| (f) Active compound of the formula I | 5.0 g |
|---|---|
| Propylene glycol | 50.0 g |
| Sodium carbonate | 5.0 g |
| Water | to 100 ml |
| (g) Active compound of the formula I | 5.0 g |
| Monoethanolamine | 10.0 g |
| N-Methylpyrrolidone | to 100 ml |
| (h) Active compound of the formula I | 2.5 g |
| Sodium carbonate | 5.0 g |
| Polyethylene glycol 200 | to 100 ml |

The active compound is dissolved in polyethylene glycol with warming and sodium carbonate is suspended therein.

EXAMPLE A

Coccidiosis in hens 9 to 11 day-old chicks were infected with 40,000 sporulated oocysts of strongly virulent strains of *Eiveria acervulina, E. maxima* and *E. tenella*, the disease initiators of intestinal coccidiosis.

3 days before infection and 8 days after infection (end of the test), active compound was administered mixed into the feed of the animals in the concentration indicated.

The number of oocysts in the faeces was determined with the aid of the McMaster chamber (see Engelbrecht and coworkers "Parasitologische Arbeitsmehoden in Medizin und Veterinärmedizin" (Parasitological Working Methods in Medicine and Veterinary Medicine), p. 172, Akademie-Verlag, Berlin (1965)).

Those bases are regarded as active which prevent completely or to a great extent the excretion of oocysts and/or the clinical symptoms of coccidiosis including mortality. The active doses are indicated in the following table:

TABLE 1

| | | | Coccidiosis in hens | | |
|---|---|---|---|---|---|
| Example No. | Dose ppm. | Death rate dead/ employed | Oocyst excretion in % in comparison with the untreated infected control | Weight increase in % in comparison with the non-infected untreated control | Blood excretion with the faeces |
| untreated infected control | | 2/6 | 100 | 35 | heavy |
| 1 | 50 | 0/3 | 0 | 100 | none |

PREPARATION EXAMPLES

I. Examples of process 2a

Example 1

2,6-Dichloro-α-(4-chlorophenyl)-4-(1-uracil)-phenylacetonitrile 7.45 g (0.018 mol) of 2,6-dichloro-α-(4'-chlorophenyl-4-(3-ethoxy-acryloyl)ureido-phenylacetonitrile are dissolved in 150 ml of tert. butanol and 2.12 g (0.018 mol) of potassium tert. butoxide are added and the mixture is heated to boiling for 10 minutes. The solvent is distilled off in vacuo and the residue is heated in vacuo at 100° C.

for 30 minutes. It is then stirred with water, the mixture is acidified using acetic acid, and the precipitated solid is filtered off and recrystallized from ethanol. 6.2 g (78 % of theory) of 2,6-dichloro-α-(4-chlorophenyl)-4-(1-uracil)-phenylacetonitrile are thus obtained.

The following are prepared analogously:

Example 2

2,6-Dichloro-α-(4-trifluoromethylthio)-4-(1-uracil)-phenylacetonitrile

Example 3

2,6-Dichloro-α-(4,-trifluoromethoxy)-4-(1-uracil)-phenyl

Example 4

2,6-Dichloro-α-(4-trifluoromethylsulphonyl)-4-(1-uracil)phenylacetonitrile

Example 5

2,6-Dichloro-α-(2-benzothiazolyl)-4-(1-uracil)-phenylacetonitrile

II. Example of process 2b

Example 6

2,6-Dichloro-α-(2',4'-dichlorophenyl)-α-methyl-4-(3-N-methyl-1-uracil)-phenylacetonitrile 4.5 g (0.01 mol) of 2,6-dichloro-α-(2,',4'-dichlorophenyl)-α-methyl-4-(1-uracil)-phenylacetontrile are dissolved in 50 ml of absolute DMSO and 0.23 g 20 minutes at room temperature and 1.8 g (0.013 mol) of methyl iodide in 5 ml of DMSO are then added. The mixture is warmed to 50° C. and kept at this temperature for 6 hours, then it is concentrated in vacuo and water is added to the residue. After filtering off the precipitated solid with suction, 2.64 g (57% of theory) of the N-methyl compound are thus obtained.

Examples of process 2c

Example 7

2,6-Dichloro-α-(2',6'-dichlorophenyl)-4-(1-uracil)-phenylacetonitrile 5.6 g (0.012 mol) of 2,6-dichloro-α-(2',6'-dichlorophenyl)-4-(5'-carboxy-1'-uracil)-phenhylacetonitrile are heated to 170° C. in 10 ml of mercaptoacetic acid. After 1 hour, the mixture is allowed to cool, water is added and, after filtering off the precipitate with suction, 3.4 g (67% of theory) of 2,6-dichloro-α-(2',6'-dichlorophenyl)-4-(1'-uracil)-phenylacetonitrile are obtained.

Example 8

2,6-Dichloro-α-(4'-methylphenyl)-4-(1-uracil)-phenylacetonitrile

Example 9

2,6-Dichloro-α-(2'-pyridinyl)-4-(1-uracil)-phenylacetonitrile

Example 10

2,6-Dichloro-α-(4'-trifluoromethylphenyl)-4-(1-uracil)-phenylacetonitrile

Example of process 4

Example 11

2,6-Dichloro-α-(4'-chlorophenyl)-4-N(3-ethoxyacryloyl)-ureido-phenylacetonitrile 10.7 g (0.034 mol) of 2,6-dichloro-α-(4'-chlorophenyl)-4-aminophenylacetonitrile are dissolved in 70 ml of abs. toluene. 150 ml of a toluene solution prepared from 8.5 g of silver cyanate and 5.6 g of ethoxyacryloyl chloride are added dropwise to this and the mixture is stirred for 1 hour at 40° C. The precipitated solid is filtered off with suction washed with petroleum ether and dried. 12.6 g (82% of theory) of 2,6-dichloro-60-(4'-chlorophenyl)-4-(3-ethoxyacryloyl)ureido-phenylacetonitrile are thus obtained.

The following are prepared analogously:

Example 12

2,6-Dichloro-α-(3',4'-dichlorophenyl)-4-N(3-ethoxyacryloyl)-ureido-phenylacetonitrile

Example 13

2,6-Dichloro-α-(4'-trifluoromethoxypheny)-4-N(3-ethoxyacryloyl)-ureido-phenylacetonitrile

Example 14

2,6-Dichloro-α-(4'-trifluoromethylthiophenyl)-4-N(3-ethoxyacryloyl)-ureido-phenylacetonitrile Example of process 4b

Example 15

2,6-Dichloro-α-(4'-chlorophenyl)-4-N(3-ethoxyacryloyl)-N'-methylureido-phenylacetonitrile 8.6 g (0.025 mol) of 4-isocyanato-2,5-dichloro-α-(4-chlorophenyl)-α-methyl-phenylacetonitrile are dissolved in absolute tetrahydrofuran. 3.2 g (0.025 mol) of N-methylethoxyacrylamide are added dropwise to this and 600 mg (0.025 mol) of sodium hydroxide are then added in portions. The mixture is warmed to 40° C. for 1 h and then to 60° C. for a further 3 h. After cooling, the precipitated solid is filtered off with suction and recrystallized from ethanol. 6.2 g (52% of theory) of 2,6-dichloro-α-(4'-chlorophenyl)-4-N-(3-ethoxyacryloyl)-N'-methylureidophenylacetonitrile are thus obtained.

Example of process 6

Example 16

2,6-Dichloro-α-(4'-methylphenyl)-4-(5-carboxy-1-uracil)phenylacetonitrile 13.5 g (0.033 mol) of 2,6-dichloro-α-(4'-methylphenyl)-4-(5-carboxy-1-uracil)phenylacetonitrile are stirred under reflux 200 ml of HCl/glacial acetic acid (1:1). Water is then added and the precipitated carboxylic acid, 8.9 g (63% of theory), is filtered off with suction.

The following are prepared analogously:

Example 17

2-Chloro-α-(4'-chlorophenyl)-4-(5-carboxy-1-uracil)-phenylacetonitrile

Example 18

2,6-Dichloro-α-phenyl-4-(5-carboxy-1-uracil)-phenylacetonitrile

Example 19

2,6-Dichloro-α-(4'-methylphenyl)-4-(1-uracil)-phenylacetonitrile

12 g (0.03 mol) of cyanouracil are stirred under reflux in 50 ml of conc. HCl and 30 ml of mercaptoacetic acid for 36 hours. After cooling, the mixture is diluted with water and the precipitate which is deposited is filtered off with suction. Recrystallization from ethanol yields 7.9 g (70% of theory) of 2,6-dichloro-α-(4'-methylphenyl)-4-(1-uracil)-phenylacetonitrile.

The following are prepared analogously:

Example 20

2,6-Dichloro-α-(2'-chlorophenyl)-4-(1-uracil)-phenylacetonitrile

Example 21

2,6-Dichloro-α-(3'-methylphenyl)-4-(1-uracil)-phenylacetonitrile

Example 22

2,6-Dichloro-α-(2'-fluoro-6'-chlorophenyl)-4-(1-uracil)-phenyl-acetonitrile

Example of process 8

Example 23

2,6-Dichloro-α-(4'-methylphenyl)-4-(5-cyano-1-uracil)-phenylacetonitrile

17.2 g (0.038 mol) of 2,6-dichloro-α-(4'-methylphenyl)-4-[N-(2-cyanoacryloylurethane]amino-phenylacetonitrile are heated under reflux for 2 hours with 4.2 g (0.05 mol) of sodium acetate in 200 ml of ethanol. After cooling, the mixture is acidified using 2N HCl and the precipitate which is deposited is filtered off with suction. 12.2 g (74% of theory) of 2,6-dichloro-α-(4'-methylphenyl)-4-(5-cyano-1-uracil)-phenylacetonitrile are thus obtained.

The following are prepared analogously:

Example 24

2,6-Dichloro-α-(4-chlorophenyl)-4-(5-cyano-1-uracil)-phenylacetonitrile

Example 25

2,6-Dichloro-α-(4-trifluorophenyl)-4-(5-cyano-1-uracil)phenylacetonitrile

Example of process 10

Example 26

2,6-Dichloro-α-(4-methylphenyl)-4-N-(2-cyanoacryloylurethane)amino-phenylacetonitrile

25 g (0.086 mol) of 2,6-dichloro-α-(4'-methylphenyl)-4-amino-phenylacetonitrile are stirred under reflux for 4 hours with 17.8 g (0.09 mol) of N-(2-cyano-3-ethoxyacryloyl)urethane in 200 ml of ethanol. The mixture is then concentrated by half and the product is allowed to crystallize out. 28.2 g (72% of theory) of 2,6-dichloro-α-(4-methylphenyl)-4-N-(2-cyano-acryloylurethane)amino-phenylacetonitrile are thus obtained.

The following are prepared analogously:

Example 27

2,6-Dichloro-α-(4'-chlorophenyl)-4-N-(2-cyanoacryloylurethane)amino-phenylacetonitrile

Example 28

2,6-Dichloro-α-methyl-α-phenyl-4-N-(2-cyanoacryloylurethane)-amine phenylacetonitrile

It will be appreciated that the instant specification and claims are set forth by way of illustration and not limitation, and that various modifications and changes may be made without departing from the spirit and scope of the present invention.

What is claimed is:

1. A substituted uracil of the formula

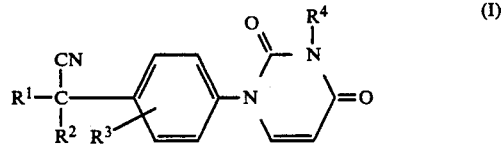

$R^1$ represents phenyl, pyridyl or benzothiazolyl, each of which is unsubstituted or substituted by one or more identical or different halogen, $C_{1-4}$-alkyl, $C_{1-4}$-halogenoalkyl, $C_{1-4}$-alkoxy, $C_{1-4}$-alkylthio, $C_{1-4}$-halogenoalkoxy, $C_{1-4}$-halogenoalkylthio, cyano, $C_{1-4}$-alkoxycarbonyl, $C_{1-4}$-alkylsulphinyl, $C_{1-4}$-alkylsulphonyl, $C_{1-4}$-halogenoalkylsulphinyl for $C_{1-4}$-halogenoalkylsulphonyl radical's $R^2$ represents H or $C_{1-4}$-alkyl, $R^3$ represents one or more identical or different hydrogen, halogen, $C_{1-4}$-alkyl or $C_{1-4}$-halogenoalkyl radicals and $R^4$ represents hydrogen.

2. A compound according to claim 1, in which $R^1$ represents phenyl which is unsubstituted or substituted by halogen, $C_{1-4}$-halogenoalkyl, $C_{1-4}$-halogenoalkylthio, $C_{1-4}$-halogenoalkoxy, $C_{1-4}$-alkyl, $C_1$-$C_4$-halogenoalkylsulphinyl, or $C_1$-$C_4$-halogenoalkylsulphonyl, $R^2$ represents H or $C_{1-4}$-alkyl, $R^3$ represents halogen, $C_{1-4}$-alkyl, or $C_{2-4}$-halogenoalkyl, and $R^4$ represents hydrogen.

3. A composition useful for combating parasitic protozoa comprising an amount effective to combat parasitic protozoa of at least one compound according to claim 1 and a suitable extender.

4. A method for combating parasitic protozoa comprising applying to said protozoa or to a parasitic protozoal environment an effective amount of at least one compound according to claim 1.

* * * * *

UNITED STATES PATENT AND TRADEMARK OFFICE
CERTIFICATE OF CORRECTION

PATENT NO. : 5,023,260

DATED : June 11, 1991

INVENTOR(S) : Lindner et al.

It is certified that error appears in the above-identified patent and that said Letters Patent is hereby corrected as shown below:

Col. 26, line 48   Delete " $C_{2-4}-$ " and substitute -- $C_{1-4}-$ --

Signed and Sealed this

Fifteenth Day of June, 1993

Attest:

MICHAEL K. KIRK

Attesting Officer     Acting Commissioner of Patents and Trademarks